(12) United States Patent
Pandiripally

(10) Patent No.: US 7,229,792 B2
(45) Date of Patent: Jun. 12, 2007

(54) METHOD OF PRODUCING RECOMBINANT PROTEINS

(76) Inventor: Vinod Pandiripally, 7621 Flint, Apt. F, Shawnee, KS (US) 66214

( * ) Notice: Subject to any disclaimer, the term of this patent is extended or adjusted under 35 U.S.C. 154(b) by 0 days.

(21) Appl. No.: 11/113,784

(22) Filed: Apr. 25, 2005

(65) Prior Publication Data

US 2005/0244928 A1    Nov. 3, 2005

Related U.S. Application Data

(60) Provisional application No. 60/567,474, filed on May 3, 2004.

(51) Int. Cl.
*C12P 21/02*    (2006.01)
*C12N 1/21*    (2006.01)

(52) U.S. Cl. .................. 435/69.1; 435/252.33

(58) Field of Classification Search ............ None
See application file for complete search history.

(56) References Cited

U.S. PATENT DOCUMENTS 5,798,099 A * 8/1998 Yuuki et al. .............. 424/185.1
5,891,710 A * 4/1999 Zimmermann et al. .. 435/252.3
5,945,522 A * 8/1999 Cohen et al. .............. 536/23.1

OTHER PUBLICATIONS

Wingfield et al., Current Protocols in Protein Science, Overview of the Purification of Recombinant Proteins Produced in *Escherichia coli*, 2002, Chapter 6.1, pp. 6.1.1-6.1.37.*
Blight et al., Heterologous Protein Secretion and the Versatile *Escherichia coli* Haemolysin Translocator, Trends in Biotechnology, 1994, vol. 12, pp. 450-455.*
Watson et al., Recombinant DNA. A Short Course, 1983, Chapter 6, Figure 6-17.*
Slade et al., Recombinant Proteins—The costs of Production in D. discoideum; use of Dictyostelium discoideum as an Alternative Host to Mammal Cell Culture, Aust. Biotechnol. Conf., 1989, 8 Meet., pp. 256-258.*
Bourot et al., Glycine Betaine-assisted Protein Folding in a lysA Mutant of *Escherichia coli*, The Journal of Biological Chemistry, 2000, vol. 275, pp. 1050-1056.*
Bosma et al., Biodegradation of 1,2,3-Trichloropropane through Directed Evolution and Heterologous Expression of a Haloalkane Dehalogenase Gene, Applied and Environmental Microbiology, 2002, vol. 68, pp. 3582-3587.*
Ohno et al., "Production of a Lipopeptide Antibiotic, Surfactin, by Recombinant *Bcillus subtilis* in Solid State Fermentation," Biotechnology and Bioengineering, vol. 47, No. 2, Jul. 20, 1995.*
Pandey et al., "Solid state fermentation for the production of industrial enzymes," Current Science (Bangalore), (Jul. 10, 1999) vol. 77, No. 1, pp. 149-162.*
Appelbaum et al., "Prokaryotic in vivo expression systems," Chapter 6 of Protein Expression: A Practical Approach, Higgins et al., Eds., Oxford University Press, 1999.*
Robinson et al., "Solid-state fermentation: A promising microbial technology for secondary metabolite production," Applied Microbiology and Biotechnology, (Apr. 2001) vol. 55, No. 3, pp. 284-289.*

* cited by examiner

*Primary Examiner*—Robert A. Wax
(74) *Attorney, Agent, or Firm*—Gerhard P. Shipley

(57) ABSTRACT

A method of producing recombinant proteins, or polypeptides, in bacteria or other host cells grown on a substantially solid, i.e., solid or semi-solid, nutrient growth medium harboring DNA sequences of interest for encoding the recombinant proteins under the control of an inducer-regulated promoter or constitutive promoter. The bacteria are harvested from the solid or semi-solid nutrient medium and the desired recombinant protein is recovered by disrupting the surface of the bacteria.

15 Claims, 2 Drawing Sheets

METHOD OF PRODUCING RECOMBINANT PROTEINS

RELATED APPLICATIONS

Figure 1:
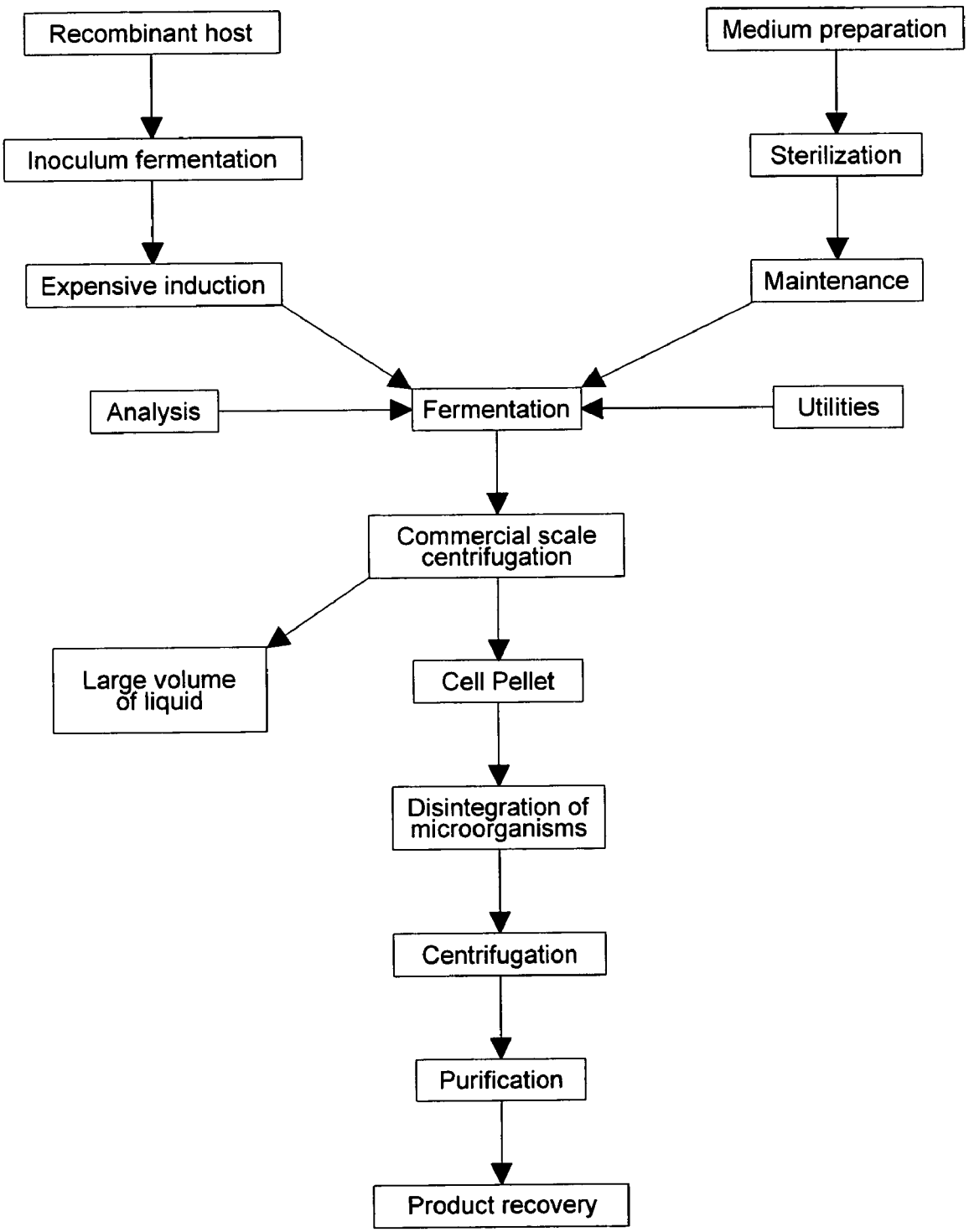

The present non-provisional application claims priority benefit, with regard to all common subject matter, of an earlier-filed U.S. provisional patent application of the same title, Ser. No. 60/567,474, filed May 3, 2004. The identified provisional application is hereby incorporated by reference into the present non-provisional application.

BACKGROUND OF THE INVENTION

1. Field of the Invention

The present invention relates broadly to methods of producing recombinant proteins. More specifically, the present invention concerns a method of producing recombinant proteins, or polypeptides, in bacteria or other host cells grown on a substantially solid, i.e., solid or semi-solid, nutrient growth medium harboring DNA sequences of interest for encoding the recombinant proteins under the control of an inducer-regulated promoter or constitutive promoter.

2. Background of the Invention

The majority of recombinant proteins, or polypeptides, currently available are produced from bacteria. *Escherichia coli* (hereinafter "*E. coli*") is by far the most frequently used organism for recombinant protein production due to its relatively lenient nutrient requirements and fast growth rate. The prior art production process, shown in FIG. 1, uses liquid media and large-scale fermentation to yield high volumes of the bacteria. Unfortunately, efficient production of recombinant proteins in bacteria, both at the diagnostic and commercial level, remains a major problem for a number of reasons including that not all recombinant proteins can be expressed to a high level with a single technology. Other obstacles include the need for expensive equipment and large culture volumes; expensive induction due to the large culture volumes; difficulty controlling pH levels and temperatures; substrate inhibition; limited oxygen transfer which results in a need for pure oxygen which is expensive and increases overall production costs; plasmid instability and loss of recombinant protein production; the presence of relatively high levels of IPTG in the cultivation medium which leads to the inhibition of the growth of the *E. coli* cells; large volumes of waste water; and difficulty in consistently reproducing batch quality. The prior art fermentation process also leads to the formation and accumulation of growth inhibiting byproducts such as acetate, a lipophilic agent that is detrimental to cell growth, which reduce growth rate and biomass yield and repress the synthesis of DNA, RNA, protein, and lipids (Jensen, E. B., and S. Carlsen. 1990 Biotechnol, Bioeng. 36: 1-11).

Due to these and other problems and limitations in the prior art, an improved method of producing recombinant proteins is needed.

SUMMARY OF THE INVENTION

The present invention overcomes the above-described problems and limitations in the prior art by providing a method of producing recombinant proteins, or polypeptides, in bacteria or other host cells grown on a substantially solid, i.e., solid or semi-solid, nutrient growth medium harboring DNA sequences of interest for encoding the recombinant proteins under the control of an inducer-regulated promoter or constitutive promoter. The bacteria are harvested from the solid or semi-solid nutrient medium and the desired recombinant protein is recovered by disrupting the surface of the bacteria.

A substantially solid nutrient growth media is inoculated with a host bacteria containing a DNA sequence which encodes a protein under the control of a promoter. Bacterial growth is allowed to proceed until the end of the incubation period. The bacteria are then removed from the media and the desired recombinant protein is recovered by disrupting the surface of the bacteria.

The host bacteria may comprise a first nucleic acid molecule (DNA) encoding a partner protein fused to a second nucleic acid molecule encoding the desired recombinant protein, resulting in a gene partner/fusion construct; or the host bacteria may comprise a first nucleic acid molecule encoding the desired recombinant protein fused with a second nucleic acid molecule encoding a partner protein; or the host bacteria may comprise a nucleic acid molecule encoding the desired recombinant protein.

The growth medium may include, for example, isopropyl-β-D-thiogalactopyranoside (IPTG) or betaine. The host bacteria may be grown on the growth medium for constitutive expression of the recombinant protein in cytoplasm, or the protein may be exported into the periplasm of the host bacteria.

The method may further include the step of inserting a gene fusion or gene construct into a chromosome of the host bacteria, or, more specifically, in an expression vector, in order to produce a transformed host cell, wherein the transformed host cell can be cultivated under any physiologically compatible conditions, such as pH or temperature, and in any suitable solid or semi-solid nutrient growth medium that supports the growth of the transformed host cell.

These and other features and advantages of the present invention are set forth in greater detail in the following detailed description of the preferred embodiment(s) and the accompanying drawings figures.

BRIEF DESCRIPTION OF THE DRAWINGS FIGURES

Figure 2:
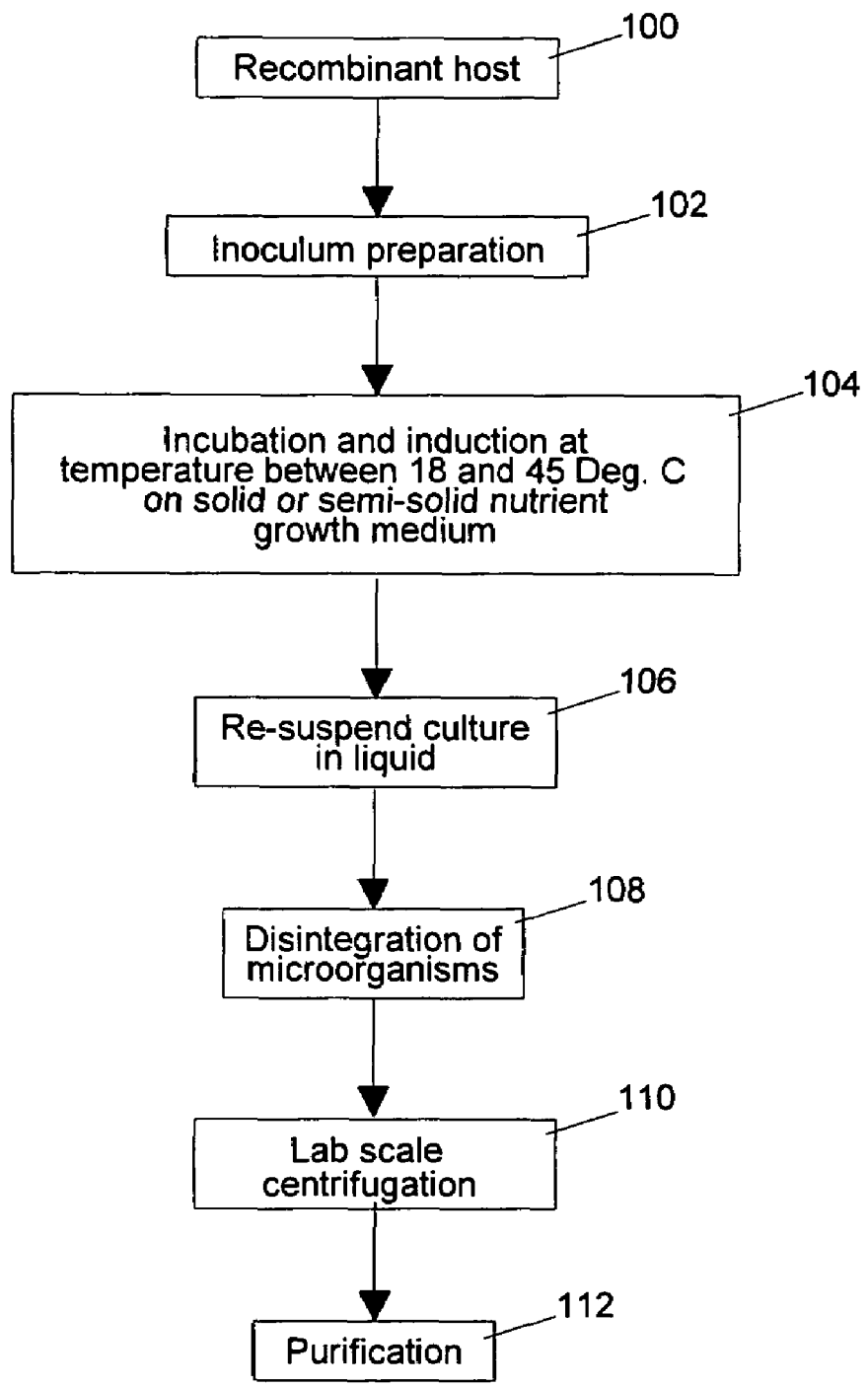

The preferred embodiment(s) of the present invention are described in detail below with reference to the following accompanying drawing figures:

FIG. 1 is a flowchart of steps involved in a PRIOR ART process using liquid media and fermentation; and FIG. 2 is a flowchart of steps involved in practicing a preferred embodiment of the method of the present invention.

DETAILED DESCRIPTION OF THE PREFERRED EMBODIMENT(S)

With reference to the various drawing figures, a method of producing recombinant proteins is herein described, shown, and otherwise disclosed in accordance with the preferred embodiment(s) of the present invention. Broadly, the present invention concerns a method of producing recombinant proteins, or polypeptides, in bacteria or other host cells grown on a substantially solid, i.e., solid or semi-solid, nutrient growth medium harboring DNA sequences of interest for encoding the recombinant proteins under the control of an inducer-regulated promoter or constitutive promoter. The bacteria are harvested from the solid or semi-solid nutrient medium and the desired recombinant protein is recovered by disrupting the surface of the bacteria. The method may be used to produce, for example, antigens for vaccines, hormones, enzymes, and other proteins of medical or commercial value. The method can be used, for example, to produce human tumor necrosis factor-alpha (TNF-α) (clone purchased from BioClone Inc., San Diego, Calif.) in the *E. coli* strain HB101 containing a plasmid harboring the T7 RNA polyemerase gene.

The recombinant protein is expressed along with the host cell growth. This overcomes problems associated with the prior art process in which the accretion of recombinant proteins was dependent on the medium. One of major shortcomings of the prior art process is the accumulation of the recombinant proteins as insoluble products in *E. coli* induction-based expression systems (Schein et al., 1988 BioTechnology 6:291-294; Vasina, J. A. & F. Baneyx. 1997 Protein Expr. Purif. 9:211-218.). It now seems that medium composition may affect protein folding as well. Most likely the effect is through the modulation of expression of the accessory proteins involved in protein folding. While a given chaperone only works on a subset of proteins, it is reasonable to suggest that for any given recombinant protein the set of chaperones which influences its folding may not be at sufficient levels in an *E. coli* induction-based expression system.

With reference to FIG. 2, in a preferred but non-limiting embodiment, the method of the present invention of producing recombinant proteins proceeds broadly as follows. A recombinant host bacteria, such as, for example, *E. Coli*, containing a DNA sequence which encodes a protein under the control of an inducer-regulated promoter or a constitutive promoter is obtained, as indicated by box 100. A solid or semi-solid nutrient growth media (i.e., source for carbon, nitrogen, minerals and vitamins) is inoculated with the host bacteria, as indicated by box 102. Bacterial growth is allowed to proceed at a temperature of approximately between 18° C. and 45° C., or other appropriate temperature range, at least until the end of the incubation period, as indicated by box 104. The bacteria are removed, or "harvested", from the growth media by suspending them in liquid, as indicated by box 106. The desired recombinant protein is recovered by disrupting the surface of the bacteria, as indicated by box 108. The result is centrifuged, as indicated by box 110. Lastly, the desired proteins are purified using any suitable purification technique, as indicated by box 112.

The host bacteria may comprise a first nucleic acid molecule (DNA) encoding a partner protein operatively fused to a second nucleic acid molecule encoding the desired recombinant protein, resulting in a gene partner/fusion construct; or the host bacteria may comprise a first nucleic acid molecule encoding the desired recombinant protein fused with a second nucleic acid molecule encoding a partner protein; or the host bacteria may comprise a nucleic acid molecule encoding the desired recombinant protein.

The growth medium may include, for example, IPTG at a concentration of less than approximately 25 micro-mole per milliliter. Alternatively, the growth medium may include betaine at an appropriate concentration per milliliter. A host bacteria inoculum of approximately $1.5 \times 10^7$ bacterial cells per milliliter of said bacteria containing the desired DNA insert may be added to the growth medium. The host bacteria may be grown on the growth medium for constitutive expression of the recombinant protein in cytoplasm, or the protein may be exported into the periplasm of the host bacteria.

The method may further include the step of inserting a gene fusion or gene construct into a chromosome of the host bacteria, or, more specifically, in an expression vector, in order to produce a transformed host cell, wherein the transformed host cell can be cultivated under any physiologically compatible conditions, such as pH or temperature, and in any suitable solid or semi-solid nutrient growth medium that supports the growth of the transformed host cell.

In exemplary but non-limiting use and operation, the method of the present invention was successfully implemented as follows. The growth medium was prepared using Luria agar medium containing 10 grams of tryptone, 5 grams of yeast extract, 10 grams of NaCl, and 15 grams of agar. The tryptone, yeast extract, NaCl, and agar were obtained from Difco Laboratories, Detroit, Mich. The Luria agar medium was adjusted to provide a total volume of 1 liter. The medium was sterilized in an autoclave. After the medium had cooled to approximately 47° C., an appropriate antibiotic such as kanamycin or ampicillin was added to provide a concentration of 1 micro-gram per milliliter. IPTG at a concentration of less than approximately 25 micromoles per milliliter was also added. Approximately 25 milliliters of molten Luria agar medium was then poured into each plate and was allowed to solidify at room temperature. A single colony of host bacteria having the desired DNA insert was constructed by introducing cloned human TNF-α into *E. coli* strain HB101 containing a plasmid harboring the T7 RNA polyemerase gene. The colony was suspended in approximately 1000 micro-liters of water and vigorously shaken. The resulting suspension, comprising a host bacteria inoculum of approximately $1.5 \times 10^7$ bacterial cells per milliliter of said bacteria containing the desired DNA insert, was plated on Luria agar plates containing the aforementioned antibiotic and IPTG and was allowed to incubate for approximately between 12 hours and 15 hours at approximately between 25° C. and 37° C.

The host bacteria culture was then obtained from the agar plates and harvested by centrifugation at approximately 10,000 gravities for approximately 6 minutes at approximately 4° C. The entire supernatant was removed and the cell pellet was frozen to approximately −80° C.

The desired recombinant proteins were then obtained from the host bacteria by breaking the bacterial membranes. The host bacteria may, for example, be physically sheared, such as by a French press, or chemically disrupted and the desired recombinant proteins obtained by first suspending the host bacteria in a solution, such as a buffered or saline solution, and then removing the bacterial debris from the solution containing the lysed cells and recovering the protein human TNF-α.

The protein human TNF-α was purified by affinity column chromatography. A 1 gram bacterial cell pellet yielded 2.5 milligrams of recombinant protein of human TNF-α.

From the preceding discussion, it will be appreciated that the method of the present invention provides a number of advantages over the prior art, including, for example, greatly increasing the efficiency of recombinant protein production. Other advantages include reduced investment in equipment and reduced culture volumes; elimination of expensive induction associated with large culture volumes; simple and inexpensive growth media; stable or more easily controlled physical parameters such as pH levels and temperatures; reduction or elimination of the formation of inclusion bodies and r-protein solubility; improved batch consistency and product quality; lower production costs, decreased production time, and simple and convenient scale-up; elimination or reduction in the use of expensive and toxic inducers; elimination or reduction of the need to optimize various parameters such as induction time, concentration of chemical inducer, and pre- and post-induction feeding strategy;

and avoidance of the accumulation of harmful acetate. By way of comparison, flask cultures generally provide a higher yield than high cell density cultures (i.e., fermentation) (Jeong, K. J., and S. Y. Lee. 1999 Appl. Environment. Microbiol. 65:3027-3032. and Yoon et al., 2003 Biotechnol Bioeng. 81:753-767). The method of the present invention provides equal or higher yields of biologically active recombinant proteins than flask cultures.

Although the invention has been described with reference to the preferred embodiments illustrated in the attached drawings, it is noted that equivalents may be employed and substitutions made herein without departing from the scope of the invention as recited in the claims.

Having thus described the preferred embodiment of the invention, what is claimed as new and desired to be protected by Letters Patent includes the following:

The invention claimed is:

1. A method of producing a desired recombinant protein, the method comprising the steps of:
    (a) inoculating a substantially solid nutrient growth medium with *Escherichia coli* containing a DNA sequence which encodes a protein under the control of a promoter, wherein the substantially solid nutrient growth medium includes isopropyl- [3-D-thiogalactopyranoside at a concentration of less than approximately 25 micro-moles per milliliter;
    (b) allowing the *Escherichia coli* to multiply during an incubation period; and
    (c) removing the *Escherichia coli* from the substantially solid nutrient growth medium and recovering the desired recombinant protein by disrupting a surface of the *Escherichia coli*.

2. The method as set forth in claim 1, wherein the *Escherichia coli* include a gene partner/fusion construct of a first nucleic acid molecule encoding a partner protein fused to a second nucleic acid molecule encoding the desired recombinant protein.

3. The method as set forth in claim 1, wherein the *Escherichia coli* include a first nucleic acid molecule encoding the desired recombinant protein fused to a second nucleic acid molecule encoding a partner protein.

4. The method as set forth in claim 1, wherein the *Escherichia coli* include a nucleic acid molecule encoding the desired recombinant protein.

5. The method as set forth in claim 1, wherein the *Escherichia coli* inoculum of step (a) includes approximately $1.5 \times 10^7$ *Escherichia coli* cells per milliliter.

6. The method as set forth in claim 1, wherein the promoter is an inducer-regulated promoter.

7. The method as set forth in claim 1, wherein the promoter is a constitutive promoter.

8. The method as set forth in claim 1, wherein the *Escherichia coli* are allowed to multiply in step (b) at a temperature of approximately between 18° C. and 45° C.

9. The method as set forth in claim 1 wherein the substantially solid nutrient growth medium includes betaine.

10. The method as set forth in claim 1, wherein the *Escherichia coli* are grown on the substantially solid nutrient growth medium for constitutive expression of the desired recombinant protein in cytoplasm.

11. The method as set forth in claim 1, wherein the *Escherichia coli* are grown on the substantially solid nutrient growth medium for constitutive expression of the desired recombinant protein exported into the periplasm of the *Escherichia coli*.

12. The method as set forth in claim 1, further including the step of inserting a gene fusion or gene construct into a chromosome of the *Escherichia coli* in order to produce transformed *Escherichia coli*, wherein the transformed *Escherichia coli* can be cultivated under substantially any physiologically compatible conditions and in substantially any suitable solid nutrient growth medium that supports growth of the transformed *Escherichia coli*.

13. A method of expressing a desired recombinant protein, the method comprising the steps of:
    (a) inoculating a substantially solid nutrient growth medium with *Escherichia coli* containing a DNA sequence which encodes a protein under the control of a promoter, wherein the substantially solid nutrient growth medium includes isopropyl-13-D-thiogalactopyranoside at a concentration of less than approximately 25 micro-moles per milliliter;
    (b) allowing the *Escherichia coli* to multiply on the substantially solid nutrient growth medium during expression of the desired recombinant protein; and
    (c) recovering the desired recombinant protein from the *Escherichia coli*.

14. A method of expressing a desired recombinant protein, the method comprising the steps of:
    (a) inoculating a solid nutrient growth medium with *Escherichia coli* containing a DNA sequence which encodes a protein under the control of a promoter, wherein the solid nutrient growth medium includes isopropyl-13-D-thiogalactopyranoside, at a concentration of less than approximately 25 micro-moles per milliliter, and betaine;
    (b) allowing the *Escherichia coli* to multiply on the solid nutrient growth medium during expression of the desired recombinant protein; and
    (c) removing the *Escherichia coli* from the solid nutrient growth medium and recovering the desired recombinant protein by disrupting a surface of the *Escherichia coli*.

15. A method of producing a desired recombinant protein in a large quantity, the method comprising the steps of:
    (a) inoculating a substantially solid nutrient growth medium with *Escherichia coli* containing a DNA sequence which encodes a protein under the control of a promoter;
    (b) allowing the *Escherichia coli* to multiply during an incubation period; and
    (c) removing the *Escherichia coli* from the substantially solid nutrient growth medium and recovering the large quantity of the desired recombinant protein by disrupting a surface of the *Escherichia coli*.

* * * * *

UNITED STATES PATENT AND TRADEMARK OFFICE
CERTIFICATE OF CORRECTION

PATENT NO. : 7,229,792 B2
APPLICATION NO. : 11/113784
DATED : June 12, 2007
INVENTOR(S) : Vinod Pandiripally It is certified that error appears in the above-identified patent and that said Letters Patent is hereby corrected as shown below:

In claim 1, line 24:
"isopropyl- [3-D-thioglactopyranoside" should read
--isopropyl-β-D-thioglactopyranoside--

In claim 5, line 47:
"1.5x107" should read
--1.5x$10^7$--

In claim 13, line 21:
"isopropyl-13-D-thioglactopyranoside" should read
--isopropyl-β-D-thioglactopyranoside--

In claim 14, line 35:
"isopropyl– 13-D-thioglactopyranoside" should read
--isopropyl-β-D-thioglactopyranoside--

Signed and Sealed this

Twenty-eighth Day of August, 2007

JON W. DUDAS
*Director of the United States Patent and Trademark Office*